United States Patent
Schmidt et al.

(10) Patent No.: US 6,458,905 B1
(45) Date of Patent: Oct. 1, 2002

(54) COMPLEXES OF PYRIDLDIIMINES WITH VANADIUM AND OTHER TRANSITION METALS, AND THEIR USE AS OLEFIN OLIGOMERIZATION AND POLYMERIZATION CATALYSTS

(75) Inventors: Roland Schmidt, Bartlesville, OK (US); Ulrich Hammon, Nürnberg (DE); M. Bruce Welch, Bartlesville, OK (US); Helmut G. Alt, Bayreuth (DE); Bryan E. Hauger, Claremore; Ronald D. Knudsen, Bartlesville, both of OK (US)

(73) Assignee: Phillips Petroleum Company, Bartlesville, OK (US)

( * ) Notice: Subject to any disclaimer, the term of this patent is extended or adjusted under 35 U.S.C. 154(b) by 64 days.

(21) Appl. No.: 09/640,285

(22) Filed: Aug. 16, 2000

Related U.S. Application Data

(60) Provisional application No. 60/149,135, filed on Aug. 16, 1999.

(51) Int. Cl.$^7$ .............................. C08F 4/16; C08F 4/22; C08F 4/20

(52) U.S. Cl. ...................... 526/172; 526/165; 526/348; 502/103; 502/167

(58) Field of Search ................................. 526/165, 172, 526/348; 502/103, 167

(56) References Cited

FOREIGN PATENT DOCUMENTS

WO    WO 99/12981    *  3/1999

OTHER PUBLICATIONS

Reardon et al., "Life and Death of an Active Ethylene Polymerization Catalyst. Ligand Involvement in Catalyst Activation. Isolation and Characterization of Two Unprecendented Neutral and Anionic Vanadium (I) /Alkyls", J. Am. Chem. Soc. 1999, 121, 9318–9325.*

* cited by examiner

Primary Examiner—David W. Wu
Assistant Examiner—Caixia Lu
(74) Attorney, Agent, or Firm—McDermott, Will & Emery

(57) ABSTRACT

A polymerization process for polymerizing at least one olefin in the presence of a pyridyldiimine metal complex as a catalyst having one of the following structures:

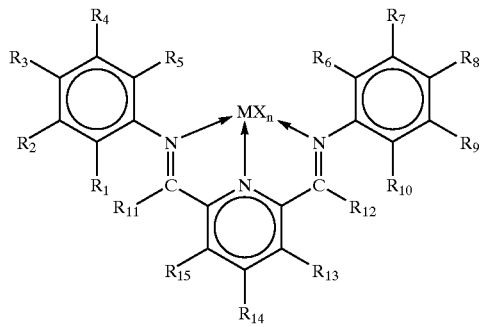

Complex I

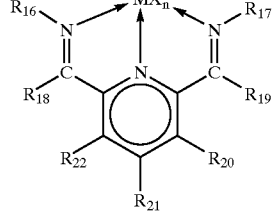

Complex II

The metal M of the complex is a transition metal from Group 4b, 5b or 6b of the Periodic Table such as vanadium. The invention also relates to the use of these metal complexes as olefin polymerization or oligomerization catalysts, optionally in combination with metal alumoxane and similar catalyst activators.

1 Claim, No Drawings

COMPLEXES OF PYRIDLDIIMINES WITH VANADIUM AND OTHER TRANSITION METALS, AND THEIR USE AS OLEFIN OLIGOMERIZATION AND POLYMERIZATION CATALYSTS

CROSS-REFERENCE TO RELATED APPLICATIONS

This application claims the priority of a provisional application, U.S. Ser. No. 60/149,135, filed Aug. 16, 1999. The entire content of this provisional application is incorporated by reference in this specification.

BACKGROUND OF THE INVENTION

The present invention relates generally to pyridyldiimine ligands having one of the following structures:

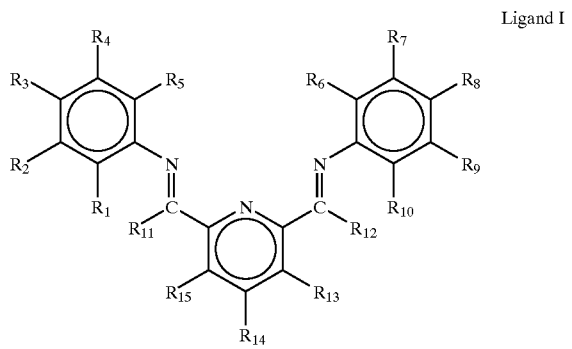

Ligand I

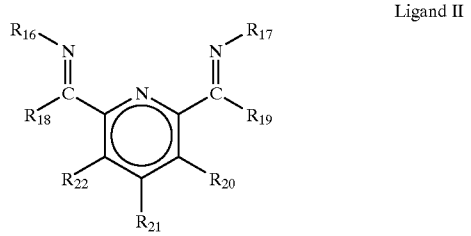

Ligand II

The invention also relates generally to pyridyldiimine metal complexes having one of the following structures:

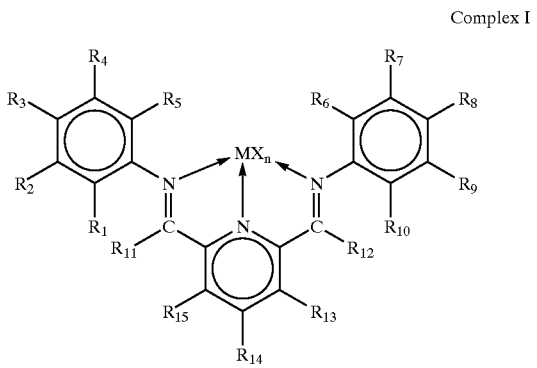

Complex I

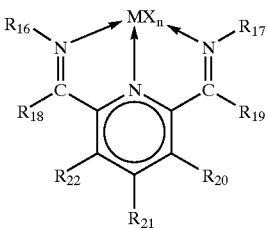

Complex II for example the Group 4b, 5b, and 6b transition metal (M) complexes. The invention also relates to the use of these metal complexes as olefin polymerization or oligomerization catalysts.

Reardon, Damien, et al., Life and Death of an Active Ethylene Polymerization Catalyst, Ligand Involvement in Catalyst Activation and Deactivation. Isolation and Characterization of Two Unprecedented Neutral and Anionic Vanadium(I) Alkyls, *JOURNAL OF THE AMERICAN CHEMICAL SOCIETY*, dated Sep. 23, 1999, Vol. 121, No. 40, pp. 9318–9325, discloses the complex identified as {2,6-bis[2,6-(I-Pr) $_2$PhN=C(Me)]$_2$(C$_5$H$_3$N)}VCl$_3$. 1.3 (CH$_2$Cl$_2$). This complex corresponds to Complex I as shown here, in which $R_1$, $R_5$, $R_6$, and $R_{10}$ are isopropyl; $R_{11}$–$R_{12}$ are methyl; $R_2$–$R_4$, $R_7$–$R_9$, and $R_{13}$–$R_{15}$ are hydrogen; M is vanadium, X is chloride, and n is 3. The substituents for this species are identified in Table II of this specification as Species 41. This complex is disclosed by Reardon et al. to be a diimine/pyridine ligand complexed with vanadium trichloride.

Reardon et al. states that reaction of this complex with a stoichiometric amount of methyl alumoxane (also known as partially methylated aluminum oxide or PMAO) in toluene resulted in an olefin polymerization catalyst that produced polyethylene having a molecular weight of 67,400 atomic mass units and a high polydispersity. Reardon et al. also identifies the corresponding Ligand I, the substituents for which are identified in the column "Reardon" in Reference Table 1 of this specification.

U.S. Pat. No. 5,714,556, issued Feb. 3, 1998 to Johnson et al., e.g. col. 22, lines 20–25, discloses 2,6-bis[4-trifluoromethyl-PhN=C(Me)]$_2$(C$_5$H$_3$N), which has the structure of Ligand I, in which $R_3$ and $R_8$ are —CF$_3$; $R_{11}$ and $R_{12}$ are methyl; and $R_1$–$R_2$, $R_4$–$R_7$, $R_9$–$R_{10}$, and $R_{13}$–$R_{15}$ are hydrogen. See "Johnson" in Reference Table 1. Johnson et al. states that this compound was "ineffective in catalyzing the polymerization of ethylene under the conditions described for Examples 23–66." Col. 20, lines 25–29.

Britovsek, George J. P., et al., Novel Olefin Polymerization, Catalysts Based on Iron and Cobalt, *CHEM. COMMUN.*, 1998 p. 849 (Brit. I), discloses the use of iron and cobalt complexes of these ligands:

2,6-bis[2,6-diisopropyl-PhN=C(methyl)]$_2$(C$_5$H$_3$N)
2,6-bis[2,6-dimethyl-PhN=C(methyl)]$_2$(C$_5$H$_3$N)
2,6-bis[2,4,6-trimethyl-PhN=C(methyl)]$_2$(C$_5$H$_3$N)
2,6-bis[2,4-dimethyl-PhN=C(methyl)]$_2$(C$_5$H$_3$N)
2,6-bis[2,6-dimethyl-PhN=CH]$_2$(C$_5$H$_3$N).

Referring to the structure of Complex I, the R substituents for these compounds are believed to be, respectively, as follows:

$R_1$, $R_5$, $R_6$, and $R_{10}$ are isopropyl; $R_{11}$ and $R_{12}$ are methyl; and $R_2$–$R_4$, $R_7$–$R_9$, and $R_{13}$–$R_{15}$ are hydrogen (i.e. "Brit.-I-1" in Reference Table 1);

$R_1$, $R_5$, $R_6$, and $R_{10}$–$R_{12}$ are methyl; $R_2$–$R_4$, $R_7$–$R_9$, and $R_{13}$–$R_{15}$ are hydrogen (Brit. I-2 in Reference Table 1);

$R_1$, $R_3$, $R_5$, $R_6$, $R_8$ and $R_{10}$–$R_{12}$ are methyl; $R_2$, $R_4$, $R_7$, $R_9$, and $R_{13}$–$R_{15}$ are hydrogen (Brit. I-3 in Reference Table 1);

$R_1$, $R_3$, $R_6$, $R_8$, $R_{11}$, and $R_{12}$ are methyl; $R_2$, $R_4$, $R_5$, $R_7$, $R_9$, $R_{10}$, and $R_{13}$–$R_{15}$ are hydrogen (Brit. I-4 in Reference Table 1);

$R_1$, $R_5$, $R_6$, and $R_{10}$ are methyl; $R_2$–$R_4$, $R_7$–$R_9$, and $R_{11}$–$R_{15}$ are hydrogen (Brit. I-5 in Reference Table 1).

Brit. I discusses olefin oligomerization or polymerization using these complexes in MAO-activated catalysts.

Britovsek, George J. P., et al., Iron and Cobalt ethylene Polymerization Catalysts Bearing 2,6-Bis(Imino)Pyridyl Ligands: Synthesis, Structures, and Polymerization Studies, *JOURNAL OF THE AMERICAN CHEMICAL SOCIETY* 121 (38) 1999, 8728-40 (indicating publication on the web on Jul. 7, 1998) (Brit. II) discloses the production of Brit I-1 Brit I-2, 3, Brit II-3, as identified in Reference Table 1. Brit. II discloses the preparation of these compounds by refluxing the starting aniline and 2-6-diacetyl pyridine in ethanol and glacial acetic acid, and reports a 60% to 80% yield.

Small, Brooke L., et al., Highly Active Iron and Cobalt Catalysts for the Polymerization of Ethylene, *JOURNAL OF THE AMERICAN CHEMICAL SOCIETY*, dated Apr. 14, 1998, vol. 120, No. 16, pp. 4049–4050 (Small I), shows iron and cobalt complexes of three ligands in which, respectively:

$R_1$, $R_5$, $R_6$, and $R_{10}$ are isopropyl; $R_{11}$ and $R_{12}$ are methyl; and $R_2$–$R_4$, $R_7$–$R_9$, and $R_3$–$R_{15}$ are hydrogen (Small I-1 in Reference Table 1);

$R_1$, $R_5$, $R_6$, $R_{10}$–$R_{12}$ are methyl; and $R_2$–$R_4$, $R_7$–$R_9$, and $R_{13}$–$R_{15}$ are hydrogen (Small I-2 in Reference Table 1); and $R_1$ and $R_6$ are t-butyl; $R_{11}$–$R_{12}$ are methyl; and $R_2$–$R_5$, $R_7$–$R_{10}$, and $R_{13}$–$R_{15}$ are hydrogen (Small I-3 in Reference Table 1). These complexes are said to be used as ethylene polymerization catalysts.

Alyea, E. C., et al., Terdentate AWN Donor Ligands Derived From 2,6-Diacetvlpyridine, *SYN. REACT. INORG. METAL-ORG. CHEM.*, 1974, 4(6), 535–544, describes a method of synthesizing pyridine-bis-(benzylimine) ligands from aniline or benzylamine and 2,6-diacetylpyridine, and their conversion to nickel and zinc complexes. At page 536, Alyea et al. describes one phenyl-substituted 2,6-diacetylpyridine represented by Ligand I (for which $R_1$–$R_{10}$ and $R_{13}$–$R_{15}$ are hydrogen and $R_{11}$–$R_{12}$ are methyl: see Alyea 1 in Reference Table 1) and one p-methoxyphenyl ligand represented by Ligand I (for which $R_3$ and $R_8$ are methoxy moieties; $R_{11}$–$R_{12}$ is methyl, and $R_1$–$R_2$, $R_4$–$R_7$, $R_9$–$R_{10}$; and $R_{13}$–$R_{15}$ are hydrogen: see Alyea 2 in Reference Table 1). The benzyl-substituted ligands and complexes described in Alyea are understood to differ from Ligand I and Complex I by the presence of a methylene linkage between each phenyl moiety and the associated nitrogen atom—they are made from benzylamine or its derivative, instead of from an aniline derivative. These ligands are represented by Ligand II, in which $R_{16}$ and $R_{17}$ are benzyl (phenylmethyl) moieties, $R_{18}$ and $R_{19}$ are methyl moieties, and $R_{20}$–$R_{22}$ are hydrogens: see Alyea 3 in Reference Table 2.

Small, Brooke L. et al., Iron-Based Catalysts with Exceptionally High Activities and Selectivities for Oligomerization of Ethylene to Linear α-Olefins, *JOURNAL OF THE AMERICAN CHEMICAL SOCIETY* 120 1998, 7143–7144 (Small II), discloses iron complexes with ligands of Complex I in which, for respective compounds:

$R_1$ $R_6$, $R_{11}$ and $R_{12}$ are methyl and $R_2$–$R_5$, $R_7$–$R_{10}$, and $R_{13}$–$R_{15}$ are hydrogen: see Small II-1 in Reference Table 1;

$R_1$ and $R_6$ are ethyl; $R_{11}$ and $R_{12}$ are methyl; and $R_2$–$R_5$, $R_7$–$R_{10}$, and $R_{13}$–$R_{15}$ are hydrogen: see Small II-2 in Reference Table 1; and $R_1$ and $R_6$ are isopropyl; $R_{11}$ and $R_{12}$ are methyl; and $R_2$–$R_5$, $R_7$–$R_{10}$, and $R_{13}$–$R_{15}$ are hydrogen: see Small I-3 in Reference Table 1.

Small II reports that "by reducing the steric bulk of these pyridinebisimine ligands the resulting iron catalysts oligomerize ethylene to linear α-olefins with exceptionally high turnover frequencies . . . and selectivities." Specifically, the steric bulk at $R_1$ and $R_6$ is being reduced. The ligands are said to be synthesized by reacting an excess of the aniline analog and 2,6-diacetylpyridine in methylene chloride or methyl alcohol, in the presence of formic acid for 40 hours, then working up the product. Yields of 55–67% are reported.

U.S. Pat. No. 5,817,651, issued Oct. 9, 1998 (D'Ambra et al.) discloses the preparation of 3-[(1-phenylimino)ethyl] pyridine by reacting 3-acetyl pyridine and aniline in a toluene solvent, in the presence of glacial acetic acid (Preparation 10). The reaction is refluxed for three days, collecting water in a Dean-Stark water trap, and then worked up.

U.S. Pat. No. 5,869,592, issued to Gagne et al. on Feb. 9, 1999, reports the use of p-toluenesulfonic acid as a catalyst for the reaction of an amine and succinic anhydride in a toluene solvent, under reflux, using a Dean-Stark trap to collect water. U.S. Pat. No. 4,391,826, issued to Mills et al., discloses the reaction of a ketone with an amine to form the corresponding imine Schiff base, in a benzene or toluene solvent, in the presence of a p-toluenesulfonic acid catalyst.

There is a continuing need in the catalyst art for catalysts having both a high activity and a high selectivity for the production of desired products such as 1-hexene. Selectivity both respecting the chain length of the oligomers produced and the proportion of α-olefins (as opposed to olefins with β, γ, and other interior unsaturation) is desired.

BRIEF SUMMARY OF THE INVENTION

One object of the invention is to provide novel ligands having the structures shown as Ligand I and Ligand II.

Another object of the invention is to provide novel metal-ligand complexes having the structures shown as Complex I and Complex II.

An additional object of the invention is to provide an improved method for synthesizing compounds according to Ligand I and Ligand II.

Still another object of the invention is an improved method for synthesizing compounds according to Ligand I and Ligand II in higher yields than have previously been achieved.

A further object of the invention is to provide metal complex catalysts for oligomerization or polymerization of α-olefins.

A still further object of the invention is to provide a metal complex activated by a methylaluminoxane, forming catalysts for oligomerization or polymerization of α-olefins.

Yet another object of the invention is to prepare high-purity higher α-olefin oligomers (such as α-butene or α-hexene) and polymers.

One or more of the preceding objects, or one or more other objects which will become plain upon consideration of the present specification, are satisfied in whole or in part by the invention described herein.

One aspect of the invention is a novel ligand having one of the following structures:

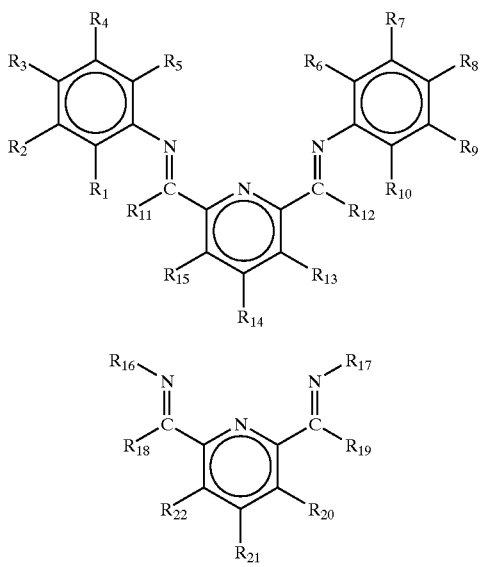

Ligand I

Ligand II

In these ligands, $R_1$–$R_{22}$ are independently selected from halogen; nitrile; straight or branched chain alkyl, alkenyl, alkynyl, cycloalkyl, aryl, aralkyl, or alkaryl moieties or combinations thereof, any of which optionally include substituent or linking heteroatoms of halogen, oxygen, nitrogen, silicon, phosphorus, or sulfur. The species identified in Reference Tables 1 and 2 are, however, excluded.

Another aspect of the invention is a metal-ligand complex having one of the following structures:

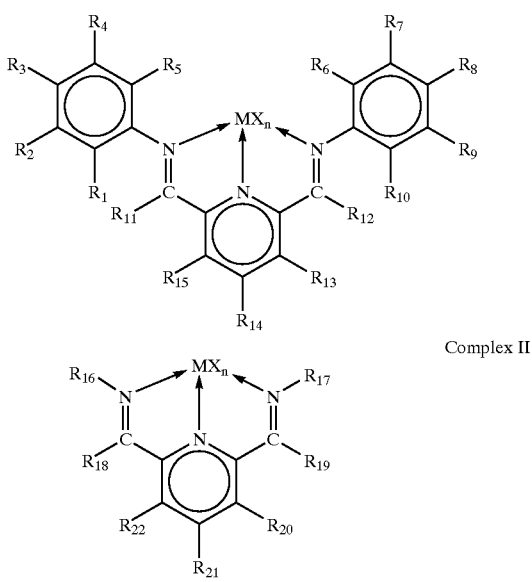

Complex I

Complex II wherein $R_1$–$R_{22}$ are as identified above, M is a metal selected from Group 4b, 5b, and 6b transition metals; X is a halide, acetyl acetonate, alkyl, dimethylamino, —CH$_2$Si(CH$_3$)$_3$, or other suitable anion; and n is 2, 3, 4, 5, or 6.

Still another aspect of the invention is a composition comprising a metal-ligand complex as identified above, combined with an amount of a methylaluminoxane effective to activate the metal-ligand complex for use as an olefin oligomerization or polymerization catalyst.

Yet another aspect of the invention is an oligomerization process comprising contacting under oligomerization conditions in a reaction zone: (a) at least one olefin; and (b) at least one catalyst having as its structure Complex I or Complex II as defined above. Certain catalysts according to the present invention are particularly selective for the production of oligomers. For the present purposes, an "oligomer" is defined as a series of at least two monomer units (four carbon atoms) and at most roughly 300 monomer units (roughly 600 carbon atoms), and which is a liquid or waxy material at room temperature. Since there is only a small difference between a 598-carbon moiety and a 602-carbon moiety, this upper limit on the size of an oligomer is not a critical limitation.

Even another aspect of the invention is a polymerization process comprising contacting at least one olefin and at least one catalyst as identified above are brought together under polymerizing conditions in a reaction zone. Certain catalysts according to the present invention are selective for the production of polymers. For the present purposes, a "polymer" is defined as a series of more than about 300 monomer units (more than 600 carbon atoms).

Another aspect of the invention is a method of forming the pyridyldiimine Ligands I or II in claim 1. A first starting material of the following structure is provided:

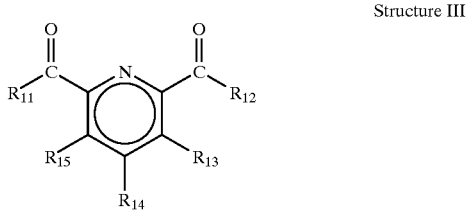

Structure III wherein $R_{11}$–$R_{15}$ are independently defined as before. A second starting material includes at least one compound having the structure:

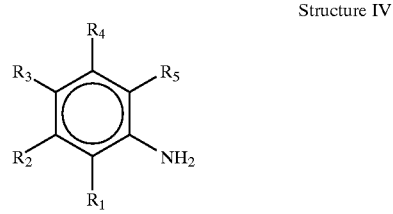

Structure IV wherein $R_1$–$R_5$ for each compound of Structure IV are independently defined as in claim 1, or $R_{16}NH_2$. These first and second starting materials are reacted in the presence of a catalytic amount of para-toluenesulfonic acid.

Even another aspect of the invention is the product produced by the foregoing oligomer production process, having a 1-hexene purity of at least about 80%.

DETAILED DESCRIPTION OF THE INVENTION

While the invention will be described in connection with one or more embodiments, it will be understood that the invention is not limited to those embodiments. On the contrary, the invention includes all alternatives, modifications, and equivalents as may be included within the spirit and scope of the appended claims.

Description of Pyridyldiimine Ligands

The contemplated pyridyldiimine ligands each have the structure of Ligand I or Ligand II as defined in this specification.

Each substituent $R_1$–$R_{22}$ is independently selected from halogens; nitrile; straight or branched chain; alkyl, alkenyl, alkynyl, cycloalkyl, aryl, aralkyl, or alkaryl moieties or combinations thereof, optionally including substituent or linking heteroatoms such as halogen, oxygen, nitrogen, silicon, phosphorus, or sulfur.

The halogen substituents contemplated here include fluorine, chlorine, iodine, or bromine.

The alkyl moieties contemplated herein include straight-chain or branched moieties having from 1 to 22 carbon atoms, alternatively from 1 to about 4 carbon atoms, optionally substituted with alkenyl, alkynyl, cycloalkyl, or aryl moieties or linkages, any of the previously mentioned heteroatoms, or both. Some examples of alkyl moieties contemplated herein include: methyl, trifluoromethyl, ethyl, oxyethyl, n-propyl, ipropyl, n-butyl, i-butyl, s-butyl, t-butyl, hexyl, octyl, decyl, dodecyl, tetradecyl, hexadecyl, octadecyl, or eicosyl moieties. Some examples of alkenyl moieties include vinyl and halogen-substituted vinyl moieties. An alkynyl moiety is any alkyl moiety having a triple carbon-carbon bond, such as an ethynyl moiety. Some examples of cycloalkyl moieties include cyclohexyl and cyclopentadienyl moieties.

The aryl moieties contemplated herein include monocyclic and polycyclic aryl moieties having from three to 28 carbon atoms, optionally substituted by nitrogen ring atoms (such as pyridinyl or diazinyl, or triazinyl) or any of the other heteroatoms or moieties identified or suggested by this disclosure or known to a skilled person. Exemplary aryl moieties are phenyl, phenylene, phenyl substituted by any of the other substituents mentioned, indicated, or suggested in this disclosure, phenylmethyl, ethylphenyl, naphthyl (optionally substituted by any of the other substituents mentioned, indicated, or suggested herein), anthracenyl (optionally substituted by any of the other substituents mentioned, indicated, or suggested herein), benzylidene, or others.

As indicated above, aralkyl and alkaryl moieties are also contemplated herein, optionally substituted or linked by heteroatoms. Examples of aralkyl moieties are benzyl, benzylamino, 2-phenylethyl, 2-ethylphenyl, and others. Examples of alkaryl moieties are methylphenyl, aminobenzyl, and others. The same moiety is either an alkaryl or an aralkyl moiety, depending on how it is attached as a substituent to the generic structure.

Some particular substituents contemplated for $R_1$–$R_{10}$ include allyl, amino, amido, acetamido, chloro, bromo, iodo, fluoro, any alkyl or aryl as previously defined such as methyl or ethyl, methoxy, ethoxy, butoxy, benzyl, nitro, nitrile, hydroxy, carboxy, formyl, acetyl, amide, methyl ester, ethyl ester, ether, mercapto, methylthio, organosilanes, or others.

In some embodiments contemplated herein, the two aniline rings on one molecule of Complex I are identical, so $R_1$–$R_5$ are respectively the same as $R_6$–$R_{10}$. In other embodiments contemplated herein, the respective aniline rings on one molecule of Complex I are differently substituted, leading to non-symmetrical products. In still other embodiments contemplated herein, one or both of the aniline reactants is replaced by a substituted or polycyclic analog of aniline, such as 1-aminoanthracene or 1-aminonaphthalene, thus replacing the aniline ring of the ligand accordingly.

In some embodiments contemplated herein, the 2 and 6 substituents on the pyridine ring are the same, so $R_{11}$ and $R_{12}$ are the same. Substituted pyridines are also contemplated in which the substituent at the 2 position is different from the substituent at the 6 position, so $R_{11}$ and $R_{12}$ are different. For example, the methyl group of one or both of the acetyl groups defining $R_{11}$ and $R_{12}$ can be replaced by hydrogen or any of the previously defined alkyl moieties, halogens, alkoxides, or amides. Some of the substituents contemplated for the pyridine ring (any of $R_{13}$–$_{15}$) include allyl, amino, amido, acetarhido, chloro, bromo, iodo, fluoro, any alkyl or aryl as previously defined such as methyl or ethyl, methoxy, ethoxy, butoxy, benzyl, nitro, nitrile, hydroxy, carboxy, formyl, acetyl, amide, methyl ester, ethyl ester, ether, mercapto, methylthio, or others.

$R_{16}$ or $R_{17}$ can be any of the previously named substituents. Aryl or alkaryl-substituted moieties, such as phenyl, naphthyl, anthracenyl, and others are contemplated, for example. Alkyl substitution at one or both of the positions adjacent to each linkage of the ring to the nitrogen atom are specifically contemplated herein, as well as other substitutions analogous to $R_1$–$R_5$ or $R_6$–$R_{10}$ on the first generic formula.

$R_{18}$ and $R_{19}$ of Ligand II are analogous to $R_{11}$–$R_{12}$ of the first formula, and similar substituents are contemplated. $R_{20}$–$R_{22}$ of Ligand II are analogous to $R_{13}$–$R_{15}$ of the first formula, and similar substituents are contemplated.

Each column of Table I characterizes the substituents $R_1$–$R_{15}$ or $R_{16}$–$R_{21}$ of one species of this genus. The species are sometimes referred to below as Species 1–23, as assigned in Table I. In addition to the species specifically identified in Table I, any other species within the definition of Ligand I or Ligand II is contemplated to be a suitable ligand species.

Preparation of Pyridyldiimine Ligands

The pyridyldiimine ligands of Ligand I can be prepared by reacting a ratio of 1 mol of 2,6-diacetylpyridine per 2 mols of aniline, through a Schiff-Base reaction. In this reaction, the oxygen atom on each acetyl moiety is substituted by the amine nitrogen atom of the aniline. The two amine hydrogens of aniline and the acetyl oxygen of the 2,6-diacetylpyridine form water as a byproduct. To make analogs with other $R_1$ and $R_{12}$ substituents than methyl, the terminal methyl groups of 2,6-diacetylpyridine optionally can be substituted by other $R_{11}$ and $R_{12}$ moieties. To make analogs with other $R_1$–$R_5$ or $R_6$–$R_{10}$ substituents than hydrogen, the hydrogen atoms in positions 2 through 6 of the aniline rings can be substituted by other $R_1$–$R_5$ or $R_6$–$R_{10}$ moieties.

The reaction of aniline and acetyl-substituted pyridine or their analogs can be carried out by refluxing the starting materials in absolute ethanol and glacial acetic acid in a water separator until no more water separates. This reaction has been found to lead to roughly a 50% yield of the desired ligand when an unsubstituted aniline is reacted (and to (generally) lower yields when a substituted aniline is reacted).

Alternatively, the pyridyldiimine ligands of Ligand I can be prepared by refluxing the same starting materials as before (but preferably using about 300% of the stoichiometric amount of the aniline component) in toluene in the presence of a catalytic amount of para-toluenesulfonic acid. The product can be worked up by the following procedure:
1. washing the reaction mixture with a dilute aqueous solution of sodium carbonate,
2. separating and drying the organic layer,
3. washing the reaction mixture again with diethyl ether,
4. combining the dried organic layers, 5. evaporating the solvents from the combined organic layers, and
6. crystallizing the residue in ethanol at −20° C.

This method has been found to yield about 75%–95% of the calculated amount of ligand.

The structures of representative ligands described in Table I were established by nuclear magnetic resonance spectroscopy (NMR) analysis. Specifically, $^1$H-NMR and $^{13}$C-NMR studies were done. The molecular weights of the ligands were established by mass spectroscopy (MS) analysis, in some instances. The analytical data is provided for the species in Table I.

The ligands represented by Ligand II are made analogously to those of Ligand I, except that the phenyl nuclei of the aniline starting material are replaced by the nucleus of another species, represented by $R_{16}$ and $R_{17}$ in Ligand II. For example, Species 21 of Table I has 1-anthracenyl moieties as $R_{16}$ and $R_{17}$. This moiety can be provided by using 1-aminoanthracene as a starting material, instead of aniline. The structure of Species 21 is established by the $^1$H-NMR and $^{13}$C-NMR studies reported in Table I.

Description of Pyridyldiimine/Metal Salt Complexes

The pyridyldiimine metal salt complexes each have the structure of Complex I or Complex II as described in this specification. The "R" groups are as described previously for the corresponding ligands, M is a metal, X is the anion of a metal salt, and n is the oxidation number of M. Where the anions are monovalent, n is also the number of X moieties per complex molecule.

M is a metal selected from the Group 4b, 5b, 6b, 7b, and 8 transition metals. The Group 4b (sometimes also known as Group 4) transition metals are titanium (Ti), zirconium (Zr), and hafnium (Hf). The Group 5b (sometimes also known as Group 5) transition metals are vanadium (V), niobium (Nb), and tantalum (Ta). The Group 6b (sometimes also known as Group 6) transition metals are chromium (Cr), molybdenum (Mo), and tungsten (W). The Group 7b transition metals are manganese (Mn), technetium (Tc), and rhenium (Re). The Group 8 transition metals are iron (Fe), cobalt (Co), nickel (Ni), ruthenium (Ru), rhodium (Rh), palladium (Pd), osmium (Os), iridium (Ir), and platinum (Pt). Vanadium is specifically contemplated for making pure α-oligomers selectively, when used under oligomerization conditions. Group 7b metals (such as manganese) and Group 8 metals (such as iron and cobalt) are also contemplated.

X is any suitable anion allowing the formation of a metal complex. The anions specifically contemplated are halogen (i.e. fluoride, chloride, bromide, or iodide, or less commonly astatide), acetyl acetonate, alkyl, dimethylamino, —CH$_2$Si (CH$_3$)$_3$, or other suitable anions. Other suitable anions known for use in this context are also contemplated. Chloride and bromide ions are particularly contemplated for the present complexes.

The value of n is 2, 3, 4, 5, or 6, depending on the choice of M and, for metals having more than one characteristic oxidation state, the oxidation state of the metal. Titanium has II, III, and IV (divalent, trivalent, and tetravalent) oxidation states, sometimes denoted as Ti$^{II}$, Ti$^{III}$, and Ti$^{IV}$. Zirconium and hafnium have only Zr$^{IV}$ and Hf$^{IV}$ oxidation states. Vanadium has four characteristic oxidation states: V$^{II}$, V$^{III}$, V$^{IV}$ and V$^V$. Niobium has Nb$^{III}$ and Nb$^{IV}$ oxidation states. Tantalum has as its characteristic oxidation state Ta$^V$. Chromium has three characteristic oxidation states: Cr$^{II}$, Cr$^{III}$, and Cr$^{VI}$. Molybdenum and tungsten each have one oxidation state, respectively Mo$^{VI}$ and W$^{VI}$. The specifically contemplated oxidation states for vanadium are V$^{III}$, V$^{IV}$ and V$^V$. Manganese has Mn$^{II}$, Mn$^{III}$, Mn$^{VI}$, and Mn$^{VII}$ oxidation states. Technetium, and rhenium have Tc$^{IV}$, Tc$^{VI}$, Tc$^{VII}$ Re$^{IV}$, Re$^{VI}$, and Re$^{VII}$ oxidation states. Iron, cobalt, and nickel have Fe$^{II}$, Fe$^{III}$, Co$^{II}$, Co$^{III}$, Ni$^{II}$, and Ni$^{III}$ oxidation states. Ruthenium and rhodium have Ru$^{IIII}$ and Rh$^{III}$ oxidation states. Palladium and platinum have Pd$^{II}$, Pd$^{IV}$, Pt$^{II}$, and Pt$^{IV}$ oxidation states. Osmium and iridium have Os$^{III}$, Os, Ir$^{III}$, and Ir$^{IV}$ oxidation states.

Representative examples of the complexes are identified in Table II. One specific species contemplated herein is Species 35 in Table II, which is the complex of vanadium trichloride (M=V, X=Cl, n=3) and 2,6-bis[2,6-dimethylphenylimino)ethyl]pyridine ($R_1$, $R_6$, $R_{11}$, and $R_{12}$= methyl, all other R's=hydrogen). Examples in which M is selected from vanadium, titanium, niobium, tantalum, and combinations thereof are also specifically contemplated.

Preparation of Pyridyldiimine/Metal salt Complexes

The present complexes can be made by complexing a pyridyldiimine ligand and a metal salt. The complex can be formed as follows. The ligand chosen is contacted with the metal salt chosen (MX$_n$) in diethyl ether or another suitable solvent or diluent for the complex.

Alternatively, as disclosed in Reardon et al., a solution of VCl$_3$(THF)$_3$ in anhydrous THF (tetrahydrofuran) can be treated with the ligand, heated to 70° C. for one hour and then stirred overnight at room temperature. The solvent is evaporated under reduced pressure to yield a solid that is redissolved in ethylene dichloride and allowed to stand at room temperature until the product crystallizes.

Another preparation, suggested by Britovsek et al., involves combining the ligand and salt in n-butanol at 80° C. for ten minutes, followed by recrystallizing from a layered ethylene dichloride-pentane 1:1 solution.

Any of these preparations can be varied for different species by a person skilled in the art. The conditions described here are illustrative, not exhaustive.

Description of Homogeneous Catalysts

Certain of the present pyridyldiimine/metal salt complexes find use as homogeneous catalysts for oligomerization of olefinic monomers. For example, Species 35 as identified in Table II has utility as an oligomerization catalyst when combined with methylaluminoxane (MAO) in certain different molar ratios.

Description of Heterogeneous Catalysts

The present catalysts are contemplated for use in heterogeneous systems. For example, any of the present complexes can be combined with a co-catalyst, a support, an activator, or combinations of these.

The cocatalyst or activator can be methylaluminoxane (MAO), trimethylaluminum (TMA), partially hydrolyzed trimethylaluminum (PHT), boranes, borates, zeolites or silicons with acid centers, or others. PHT is specifically contemplated. The ratio of water to TMA used to prepare MAO or PHT is contemplated to be optimized for catalysis or other useful properties.

The support for the catalyst can be an inorganic oxide, optionally a dehydrated inorganic oxide support. Particular supports contemplated herein include silica, silica-alumina, alumina, fluorided alumina, silated alumina, thoria, aluminophosphate, aluminum phosphate, phosphated silica, phosphated alumina, silica-titania, coprecipitated silica/titania, fluorided/silated alumina, and mixtures thereof.

Preparation of Heterogeneous Catalysts

The present catalysis can be carried out using any of a variety of different heterogeneous catalyst forms. For example, the present pyridyldiimine/metal salt complexes can be combined with a cocatalyst such as methylaluminoxane.

Utility

The present ligands have utility for formation of metal complexes. The metal complexes formed from the ligands and their compositions with activators are useful as catalysts for oligomerization and polymerization of ethylene and other α-olefins. The oligomers formed from ethylene are useful as monomers for polymerization of linear low-density polyethylene (LLDPE) and other polymers having side chains. The polymers are known to be useful for many purposes, such as for injection molding useful articles, for forming films that can be used directly or fabricated into useful articles, such as refuse bags, and for coating paper or board to form water-resistant sheets and articles.

Oligomerization Processes

The homogeneous oligomerization catalysts identified above are contacted with a polyolefin feedstock. Specific feedstocks contemplated herein are α-olefins having from two to about 20 carbon atoms per molecule, for example ethylene, 1-propene, 1-butene, 1-pentene, 1-hexene, 1-octene, 1-decene, 1-dodecene, 1-eicosene, and others.

The catalysts are used under oligomer forming conditions. Some representative, non-limiting conditions are the following:
1. Co-catalyst choice: MAO or MMAO;
2. Molar ratios of co-catalyst to catalyst precursor by weight: 1:1 to 100,000:1, optionally 50:1 to 10,000:1, optionally 100:1 to 2,000:1;
3. Reaction temperature: 0–300° C., optionally 20–50° C., optionally 40–100° C.;
4. Reaction pressure: 250–700 psig (about 170–490 N/cm$^2$);
5. Hydrogen gas partial pressure, as needed to control the reaction, optionally 10–10,000 psig (6.9 to about 6,900 N/cm$^2$), optionally 20–5000 psig (13.8 to about 3450 N/cm$^2$), optionally 50–1000 psig (34.5 to about 690 N/cm$^2$).

In one experiment, HT-GPC analysis showed that ethylene homogeneously catalyzed by the trivalent vanadium (V$^{III}$) complex identified as Species 30 (Table II) produced an oligomer having a number average molecular weight of 4,051 g/mol and a weight average molecular weight of 15,320 g/mol, giving a polydispersity of 3.78.

Species 30 is surprisingly more selective for oligomer formation and forms shorter oligomer chains, on average, than its Fe$^{II}$ and Fe$^{III}$ analogs. The results of the above experiment for the V$^{III}$ complex versus its Fe$^{II}$ and Fe$^{III}$ analogs is shown in Table III.

The catalysts made from complexes having one ortho position substituted on each aniline ring ($R_1$ and $R_6$ or $R_5$ and $R_{10}$) made oligomers and polymers with lower molecular weight in homogeneous and heterogeneous catalyst systems. The chain termination rate was increased compared to iron catalysts having both ortho positions substituted on each aniline ring ($R_1$, $R_5$, $R_6$, and $R_{10}$).

Substitution on the aniline rings of the complexes in the meta and para positions ($R_2$–$R_4$ and $R_7$–$R_9$) had little effect on the molecular weight of the product.

Description of Oligomeric and Polymeric Products

The oligomeric and polymeric products produced with the present catalysts have a much higher purity of a α-olefins, as opposed to α-olefins, γ-olefins, or other olefins with the double bond at another location than the a location between the first and second carbon atoms of the product molecule. In Table IV, examples are indicated where the hexane purity (the ratio of 1-hexene to other hexenes) is at least 80%, alternatively at least 85%, alternatively at least 90%, alternatively at least 95%, alternatively at least 97% by weight.

WORKING EXAMPLES

Several iron complexes analogous to the present invention and several vanadium catalysts according to the present invention were used with a MAO or MMAO co-catalyst in the ratios indicated in Table IV as ethylene addition reaction catalysts. The reaction references, catalysts, reaction materials, and reaction parameters and results are set out in Table IV.

In each case, a one-liter autoclave reactor was purged at 115° C. with nitrogen gas for at least 10–15 minutes. An aliquot of the prepared complex/MAO solution was syringed into the charge cylinder. The charge cylinder was then flushed with cyclohexane solvent to flush in the catalyst. The amount of cyclohexane used was 440 mL. The reactor was brought to room temperature and 50 psi partial pressure hydrogen gas was added, if used in a particular example.

The reactor was heated to just under the run temperature, and ethylene was introduced. The total reactor pressure used was as indicated in Table IV. Ethylene was fed on demand to maintain the pressure. After 30 minutes, the reactor was vented and the liquids and solids collected at ambient conditions.

In Table IV, the number in parentheses under the heading "Catalyst Description (Species)" shows which species listed in Table II is being used as the catalyst. "Metal" refers to the metal in the complex—iron or vanadium. "Co-cat/CAT ratio" refers to the molar ratio of the aluminum co-catalyst to the Complex I or Complex II catalyst referred to in "Catalyst Description". "H$_2$ (psig)" refers to the partial pressure of hydrogen introduced into the reactor at room temperature. "Solids" is the weight of polymeric species produced in the reaction. "C$_2$=Uptake" is ethylene uptake. "Wt. % Liquid" is calculated by subtracting the "Solids" from the C2=Uptake, then dividing the difference by C2=Uptake. "Polymer Productivity" is the productivity of the catalyst respecting the production of solid or polymeric products. "Oligomer Productivity" is the productivity of the catalyst respecting the production of liquid/waxy or oligomeric products. (In those instances where the solids were not measured, the value in the Oligomer Productivity column represents the total productivity of the catalyst for all products.)

The results under the "Productivity" headings in Table IV show that the chromium-complex hexene catalysts and the iron-complex catalysts (which are not part of the present invention) provided modest yields of oligomeric species per gram of metal in the catalyst. In a similar test, a prior art chromium catalyst produced about 16 to 42 kg of oligomers per gram of metal and essentially no polymers under the reaction conditions of the test. The analogous iron catalysts produced from less than 1 kg to, in one instance, 625 kg of oligomer per gram of metal, in most cases a negligible amount of polymer product per gram of metal, and in no case as much as 6 kg of the polymer per gram of metal.

In contrast, the vanadium catalysts according to the present invention produced over 323 kg of oligomers per gram of transition metal in the majority of instances. Two experiments, using Species 48 of Table II, produced over 1100 kg of oligomers per gram of metal. The vanadium catalysts produced less than 11 kg of polymer per gram of metal in all but one case. In that case, the catalyst produced about 126 kg of polymer and about 140 kg of oligomer per gram of transition metal. The latter run is thus aptly characterized as providing a mixed product.

The final column of Table IV shows the purity of 1-hexene produced in the reaction, measured as the production of 1-hexene as a percentage of all hexene species produced.

Table V shows oligomer distribution data for the same runs characterized in Table IV. As Table V illustrates, the product oligomers are in many cases predominantly narrow distributions. For example, run 21 (which is the same run as Run 21 on Table IV) produced, on an "area %" basis in a gas chromatography (GC) analysis, 1.94875 units (12%) butene, 33% hexene, 26% octene, 19% decene, 7% dodecene, and 4% tetradecene. (These percentages total 101% due to rounding errors.) It should also be noted that the instrumentation used in this analysis only measured the distribution of olefins up to $C_{14}$.

Thus, novel ligands and novel metal-ligand complexes have been prepared that have utility as olefin oligomerization and polymerization catalysts, alone or in combination with an activator.

REFERENCE TABLE 1

| | Ligand Reference (Complex I) | | | | | |
|---|---|---|---|---|---|---|
| Substituent | Reardon; Brit. I-1; Small I-1 | Johnson | Brit I-2; Small I-2 | Brit I-3 | Brit I-4 | Brit I-5 |
| $R_1$ | —CH(CH$_3$)$_2$ | H | CH$_3$ | CH$_3$ | CH$_3$ | CH$_3$ |
| $R_2$ | H | H | H | H | H | H |
| $R_3$ | H | CF$_3$ | H | CH$_3$ | CH$_3$ | H |
| $R_4$ | H | H | H | H | H | H |
| $R_5$ | —CH(CH$_3$)$_2$ | H | CH$_3$ | CH$_3$ | H | CH$_3$ |
| $R_6$ | —CH(CH$_3$)$_2$ | H | CH$_3$ | CH$_3$ | CH$_3$ | CH$_3$ |
| $R_7$ | H | H | H | H | H | H |
| $R_8$ | H | CF$_3$ | H | CH$_3$ | CH$_3$ | H |
| $R_9$ | H | H | H | H | H | H |
| $R_{10}$ | —CH(CH$_3$)$_2$ | H | CH$_3$ | CH$_3$ | H | CH$_3$ |
| $R_{11}$ | CH$_3$ | CH$_3$ | CH$_3$ | CH$_3$ | CH$_3$ | H |
| $R_{12}$ | CH$_3$ | CH$_3$ | CH$_3$ | CH$_3$ | CH$_3$ | H |
| $R_{13}$ | H | H | H | H | H | H |
| $R_{14}$ | H | H | H | H | H | H |
| $R_{15}$ | H | H | H | H | H | H |

| | Ligand I | | | | | |
|---|---|---|---|---|---|---|
| Substituent | Small I-3; Brit II-3 | Alyea 1 | Alyea 2 | Small II-1 | Small II-2 | Small II-3 |
| $R_1$ | —C(CH$_3$)$_3$ | H | H | CH$_3$ | —CH$_2$CH$_3$ | —CH(CH$_3$)$_2$ |
| $R_2$ | H | H | H | H | H | H |
| $R_3$ | H | H | —OCH$_3$ | H | H | H |
| $R_4$ | H | H | H | H | H | H |
| $R_5$ | H | H | H | H | H | H |
| $R_6$ | —C(CH$_3$)$_3$ | H | H | CH$_3$ | —CH$_2$CH$_3$ | —CH(CH$_3$)$_2$ |
| $R_7$ | H | H | H | H | H | H |
| $R_8$ | H | H | —OCH$_3$ | H | H | H |
| $R_9$ | H | H | H | H | H | H |
| $R_{10}$ | H | H | H | H | H | H |
| $R_{11}$ | CH$_3$ | CH$_3$ | CH$_3$ | CH$_3$ | CH$_3$ | CH$_3$ |
| $R_{12}$ | CH$_3$ | CH$_3$ | CH$_3$ | CH$_3$ | CH$_3$ | CH$_3$ |
| $R_{13}$ | H | H | H | H | H | H |
| $R_{14}$ | H | H | H | H | H | H |
| $R_{15}$ | H | H | H | H | H | H |

REFERENCE TABLE 2

| Substituent | Ligand Reference Alyea 3 |
|---|---|
| $R_{16}$ | —CH$_2$—C$_6$H$_5$ |
| $R_{17}$ | —CH$_2$—C$_6$H$_5$ |
| $R_{18}$ | CH$_3$ |
| $R_{19}$ | CH$_3$ |
| $R_{20}$ | H |
| $R_{21}$ | H |
| $R_{22}$ | H |

TABLE 1

| | Ligand I Species | | | |
|---|---|---|---|---|
| Substituent | 1 | 2 | 3 | 4 |
| $R_1$ | F | Cl | Br | $CH_3$ |
| $R_2$ | H | H | H | H |
| $R_3$ | H | H | H | H |
| $R_4$ | H | H | H | H |
| $R_5$ | H | H | H | H |
| $R_6$ | F | Cl | Br | $CH_3$ |
| $R_7$ | H | H | H | H |
| $R_8$ | H | H | H | H |
| $R_9$ | H | H | H | H |
| $R_{10}$ | H | H | H | H |
| $R_{11}$ | $CH_3$ | $CH_3$ | $CH_3$ | $-CH_2-C_6H_5$ |
| $R_{12}$ | $CH_3$ | $CH_3$ | $CH_3$ | $-CH_2-C_6H_5$ |
| $R_{13}$ | H | H | H | H |
| $R_{14}$ | H | H | H | H |
| $R_{15}$ | H | H | H | H |
| Reference | 91 (Thesis p. 228) | 92 (Thesis p. 228) | 93 (Thesis p. 228) | 86 (Thesis p. 227) |
| $^1$H-NMR | 8.13(d, 1H), 7.60(d, 2H), 7.55(m, 2H), 7.05–6.90(m, 6H), 2.10(s, 6H) | 8.12(d, 1H), 7.59(d, 2H), 7.50(m, 2H), 6.92–6.87(m, 6H), 2.10(s, 6H) | 8.12(d, 1H), 7.60(d, 2H), 7.50(m, 2H), 7.40–6.88(m, 8H), 2.10(s, 6H) | 8.22(d, 1H), 7.59(t, 2H), 7.26–6.65(m, 18H), 3.96(s, 4H), 2.04(s, 6H) |
| $^{13}$C-NMR | ($C_q$): 165.5, 158.9, 150.2, 130.0 (CH): 138.9, 128.4, 128.0, 124.0, 123.6, 118.9 ($CH_3$): 16.2 | ($C_q$): 166.5, 160.9, 151.2, 129.0 (CH): 138.8, 128.8, 128.2, 124.3, 124.2, 120.0 ($CH_3$): 16.0 | ($C_q$): 168.6, 152.9, 150.2, 139.0, 128.0 (CH): 138.6, 129.6, 129.0, 127.0, 126.0, 124.8, 123.8 ($CH_2$): 29.9 ($CH_3$): 17.5 | ($C_q$): 164.6, 156.9, 152.2, 139.1, 132.6 (CH): 138.8, 129.8, 129.5, 128.5, 126.5, 125.8, 124.8, 119.0 ($CH_2$): 29.0 ($CH_3$): 17.9 |
| MS (mass spectroscopy) | 362 ($M^+$ − 6) | — | — | 493 |

| | Ligand I Species | | | |
|---|---|---|---|---|
| Substituent | 5 | 6 | 7 | 8 |
| $R_1$ | $-C_6H_5$ | $CH_3$ | $CH_3$ | $CH_3$ |
| $R_2$ | H | H | H | H |
| $R_3$ | H | H | H | H |
| $R_4$ | H | H | H | H |
| $R_5$ | H | $CH_3$ | $CH_3$ | $CH_3$ |
| $R_6$ | $-C_6H_5$ | $CH_3$ | $CH_3$ | $CH_3$ |
| $R_7$ | H | H | H | — |
| $R_8$ | H | H | H | H |
| $R_9$ | H | H | H | H |
| $R_{10}$ | H | $CH_3$ | $CH_3$ | $CH_3$ |
| $R_{11}$ | $CH_3$ | $-CH_2CH_3$ | $-C_6H_5$ | $-CH_2-C_6H_5$ |
| $R_{12}$ | $CH_3$ | $-CH_2CH_3$ | $-C_6H_5$ | $-CH_2-C_6H_5$ |
| $R_{13}$ | H | H | H | H |
| $R_{14}$ | H | H | H | H |
| $R_{15}$ | H | H | H | H |
| Reference | 95 (Thesis p. 228) | 80 (Thesis p. 226) | 83 (Thesis p. 227) | 84 (Thesis p. 227) |
| $^1$H-NMR | 8.36(d, 1H), 7.65(d, 2H), 7.53–6.65(m, 14H), 2.18(s, 6H) | 8.38(d, 1H), 7.85 (t, 2H), 7.03–6.80 (m, 6H), 2.75(q, 4H), 1.98(s, 12H), 1.44(t, 6H) | 8.32–8.27(m 6H), 7.60(d, 2H), 7.50(s, 4H), 7.01–6.88 (m, 6H), 1.98 (s, 12H) | 8.38(d, 1H), 8.08–7.84(m, 4H), 7.26–6.65 (m, 14H), 3.96 (s, 4H), 1.98(s, 12H) |
| $^{13}$C-NMR | ($C_q$): 195.0, 165.9, 165.0, 163.0, 161.2, 149.0, 146.2, 141.5, 135.9, 131.9 (CH): 138.0, 131.8–120.0(14$^x$CH), 100.0, 87.2, 35.8 ($CH_3$): 17.0 | ($C_q$): 171.4, 154.5, 148.4, 125.3 (CH): 127.9, 122.9 ($CH_2$): 23.2 ($CH_3$): 18.2, 11.3 | ($C_q$): 165.9, 152.9, 149.1, 132.0, 126.9 (CH): 139.6, 130.9, 130.0, 128.6, 126.0, 124.8 124.0, 122.8 ($CH_3$): 17.5 | ($C_q$): 168.6, 152.9, 150.2, 139.0, 128.0 (CH): 138.6, 129.6, 129.0, 127.0, 126.0, 124.8, 123.8 ($CH_2$): 29.9 ($CH_3$): 17.5 |

TABLE 1-continued

| MS (mass spectroscopy) | 465 | 397 | — | 521 |
|---|---|---|---|---|

| | Ligand I Species | | | |
|---|---|---|---|---|
| Substituent | 9 | 10 | 11 | 12 |
| $R_1$ | $CH_3$ | $-CH_2CH_3$ | $-CH_2CH_3$ | $-CH(CH_3)_2$ |
| $R_2$ | H | H | H | H |
| $R_3$ | H | H | H | H |
| $R_4$ | H | H | H | H |
| $R_5$ | $CH_3$ | $-CH_2CH_3$ | $-CH_2CH_3$ | $CH_3$ |
| $R_6$ | $CH_3$ | $-CH_2CH_3$ | $-CH_2CH_3$ | $-CH(CH_3)_2$ |
| $R_7$ | H | H | H | H |
| $R_8$ | H | H | H | H |
| $R_9$ | H | H | H | H |
| $R_{10}$ | $CH_3$ | $-CH_2CH_3$ | $-CH_2CH_3$ | $CH_3$ |
| $R_{11}$ | $-(CH_2)_2-C_6H_5$ | $CH_3$ | $-CH_2CH_3$ | $CH_3$ |
| $R_{12}$ | $-(CH_2)_2-C_6H_5$ | $CH_3$ | $-CH_2CH_3$ | $CH_3$ |
| $R_{13}$ | H | H | H | H |
| $R_{14}$ | H | H | H | H |
| $R_{15}$ | H | H | H | H |
| Reference | 85 (Thesis p. 227) | 73 (Thesis p. 226) | 82 (Thesis p. 227) | 74 (Thesis p. 226) |
| $^1$H-NMR | 8.53(d, 1H), 8.18–7.96(m, 4H), 7.26–6.81 (m, 14H), 3.70–3.54(m, 4H), 3.13–2.71(m, 4H), 2.00(s, 12H) | 8.36(d, 1H), 7.90(t, 2H), 7.12–6.70(m, 4H), 2.63–2.25 (m, 8H), 1.22–1.05 (m, 12H) | 7.90(d, 1H), 7.60(t, 2H), 7.01(m, 2H), 6.76(d, 2H), 2.75(m, 8H), 2.38(q, 8H), 1.46(t, 6H), 1.16(t, 12H) | 7.82(d, 1H), 7.18(d, 2H), 6.98–6.76(m, 6H), 2.85(sept. 2H), 2.14(s, 6H), 1.96(s, 6H), 1.21(dd, 12H) |
| $^{13}$C-NMR | ($C_q$): 168.9, 154.9, 152.2, 141.0, 126.1 (CH): 137.6, 128.6, 128.5, 126.1, 125.0, 123.3 122.8 ($CH_2$): 29.7 ($CH_3$): 18.1 | ($C_q$): 166.9, 155.1, 136.9 (CH): 147.8, 131.2, 127.7, 126.0, 125.9 123.3, 122.2, ($CH_2$): 24.6, 24.3 ($CH_3$): 16.8, 13.8, 13.0 | ($C_q$): 170.6, 156.5, 141.4, 122.3 (CH): 138.0, 133.1, 129.9, 119.9 ($CH_2$): 23.0, 19.4 ($CH_3$): 12.9, 11.4 | ($C_q$): 1.67.1, 155.2, 147.6, 136.2, 125.0 (CH): 138.4, 127.8, 123.2, 118.3, 28.3 ($CH_3$): 23.1, 22.8, 18.1, 16.8 |
| MS (mass spectroscopy) | 549 | 425 | ($M^+$ − 56 = 2 Ethyl): 397 | 453 |

| | Ligand I Species | | | |
|---|---|---|---|---|
| Substituent | 13 | 14 | 15 | 16 |
| $R_1$ | $CH_3$ | $CH_3$ | $CH_3$ | $CH_3$ |
| $R_2$ | H | H | H | H |
| $R_3$ | H | Br | $CH_3$ | $-CH_2CH_3$ |
| $R_4$ | Cl | H | H | H |
| $R_5$ | H | $CH_3$ | $CH_3$ | H |
| $R_6$ | $CH_3$ | $CH_3$ | $CH_3$ | $CH_3$ |
| $R_7$ | H | H | H | H |
| $R_8$ | H | Br | $CH_3$ | $-CH_2CH_3$ |
| $R_9$ | Cl | H | H | H |
| $R_{10}$ | H | $CH_3$ | $CH_3$ | H |
| $R_{11}$ | $CH_3$ | $CH_3$ | $-CH_2CH_3$ | $CH_3$ |
| $R_{12}$ | $CH_3$ | $CH_3$ | $-CH_2CH_3$ | $CH_3$ |
| $R_{13}$ | H | H | H | H |
| $R_{14}$ | H | H | H | H |
| $R_{15}$ | H | H | H | H |
| Reference | 79 (Thesis p. 226) | 76 (Thesis p. 226) | 81 (Thesis p. 227) | 89 (Thesis p. 228) |
| $^1$H-NMR | 8.38(d, 1H), 7.89(t, 2H), 7.25–6.64(m, 6H), 2.34(s, 6H), 2.12(d, 6H) | 8.45(d, 1H), 7.92(t, 2H), 7.23(d, 4H), 2.22(t, 6H), 2.02(s, 12H) | 8.37(d, 1H), 7.88(t, 2H), 6.88(s, 4H), 2.70–2.67(dd, 4H), 2.02(s, 18H), 1.05–0.98 (t, 6H) | 8.16(d, 1H), 7.64(d, 2H), 6.97–6.80(m, 4H), 6.40(m, 2H), 2.70(q, 4H), 2.10 (s, 6H), 2.08(s, 6H), 1.40(t, 6H) |
| $^{13}$C-NMR | ($C_q$): 167.6, 155.1, 151.2, 135.2, 125.4 (CH): 137.0, | ($C_q$): 168.0, 155.0, 147.8, 127.8, 115.7 (CH): 137.1, | ($C_q$): 171.7, 154.6, 146.0, 132.1, 125.2 (CH): 137.0, | ($C_q$): 166.9, 159.1, 152.5, 139.5, 128.9 (CH): 138.0, |

TABLE 1-continued

|  |  |  |  |  |
|---|---|---|---|---|
|  | 127.0, 124.3, 122.5, 119.4, 116.7, 113.3 ($CH_3$): 16.5, 14.7 | 130.6, 122.5 ($CH_3$): 17.9, 16.7 | 128.6, 122.8 ($CH_2$): 23.1 ($CH_3$): 20.7, 18.1, 11.3 | 130.9, 130.0, 124.8 ($CH_2$): 28.0 ($CH_3$): 18.8, 16.6, 15.7 |
| MS (mass spectroscopy) | ($M^+ - 1$): 409 | 527 | 425 | 397 |

|  | Ligand I Species | | | |
|---|---|---|---|---|
| Substituent | 17 | 18 | 19 | 20 |
| $R_1$ | —$CH(CH_3)_2$ | $CH_3$ | $CH_3$ | $CH_3$ |
| $R_2$ | H | Cl | Br | $CH_3$ |
| $R_3$ | $CH_3$ | H | $CH_3$ | H |
| $R_4$ | H | H | H | H |
| $R_5$ | H | H | $CH_3$ | H |
| $R_6$ | —$CH(CH_3)_2$ | $CH_3$ | $CH_3$ | $CH_3$ |
| $R_7$ | H | Cl | Br | $CH_3$ |
| $R_8$ | $CH_3$ | H | $CH_3$ | H |
| $R_9$ | H | H | H | H |
| $R_{10}$ | H | H | $CH_3$ | H |
| $R_{11}$ | $CH_3$ | $CH_3$ | $CH_3$ | $CH_3$ |
| $R_{12}$ | $CH_3$ | $CH_3$ | $CH_3$ | $CH_3$ |
| $R_{13}$ | H | H | H | H |
| $R_{14}$ | H | H | H | H |
| $R_{15}$ | H | H | H | H |
| Reference | 90 (Thesis p. 228) | 78 (Thesis p. 226) | 77 (Thesis p. 226) | 69 (Thesis p. 225) |
| $^1$H-NMR | 8.14(d, 1H), 7.60(d, 2H), 7.16–6.61(m, 6H), 2.85 (sept. 2H), 2.28(s, 6H), 2.10(s, 6H), 1.25(d, 12H) | 8.39(d, 1H), 7.90(t, 2H), 7.16–7.09(m, 2H), 6.92–6.81 (dt, 2H), 6.62–6.55(m, 2H), 2.34(s, 6H), 2.17(s, 6H) | 8.45(d, 1H), 7.90(t, 2H), 6.98(d, 2H), 2.39(s, 6H), 2.22(s, 6H), 2.15(s, 6H), 1.97(s, 6H) | 8.40(d, 1H), 7.87 (t, 2H), 7.12–6.52 (m, 6H), 2.30(s, 12H), 2.04(s, 6H) |
| $^{13}$C-NMR | ($C_q$): 167.1, 155.2, 147.6, 136.1, 125.0 (CH): 136.9, 127.8, 123.3, 123.3, 122.2, 28.4 ($CH_3$): 23.1, 22.9, 18.2, 16.8 | ($C_q$): 167.7, 155.1, 151.0, 131.6, 125.7 (CH): 137.1, 131.7, 131.4, 123.5, 122.6, 118.4, 118.2, 114.6 ($CH_3$): 17.4, 16.6 | ($C_q$): 167.9, 154.8, 147.1, 132.2, 125.2, 124.0 (CH): 136.7, 129.5, 122.2 ($CH_3$): 23.3, 18.3, 17.5, 16.4 | ($C_q$): 164.9, 156.1, 149.4, 133.7, 121.1 (CH): 138.4, 131.0, 124.5, 124.0, 120.0 ($CH_3$)): 20.0, 16.0, 13.8 |
| MS (mass spectroscopy) | 425 | ($M^+ - 1$): 409 | 556 | 369 |

|  | Ligand I Species | |
|---|---|---|
| Substituent | 21 | 22 |
| $R_1$ | H | H |
| $R_2$ | H | $CH_3$ |
| $R_3$ | $CH_3$ | H |
| $R_4$ | H | H |
| $R_5$ | H | H |
| $R_6$ | H | H |
| $R_7$ | H | $CH_3$ |
| $R_8$ | $CH_3$ | H |
| $R_9$ | H | H |
| $R_{10}$ | H | H |
| $R_{11}$ | $CH_3$ | $CH_3$ |
| $R_{12}$ | $CH_3$ | $CH_3$ |
| $R_{13}$ | H | H |
| $R_{14}$ | H | H |
| $R_{15}$ | H | H |
| Reference | 67 (Thesis p. 225) | 66 (Thesis p. 225) |
| $^1$H-NMR | 8.12(d, 1H), 7.76(t, 2H), 7.14–6.76(m, 8H), 2.27(s, 6H), 2.13(s, 6H) | 8.23(d, 1H), 7.86(t, 2H), 7.04–6.52(m, 6H), 2.35(s, 12H), 2.13(s, 6H) |

TABLE 1-continued

| | | |
|---|---|---|
| $^{13}$C-NMR | ($C_q$): 168.9, 161.1, 149.7, 134.1<br>(CH): 138.5, 128.1, 124.7, 119.8,<br>($CH_3$): 20.8, 170.0 | ($C_q$): 166.8, 158.8, 148.5, 138.6<br>(CH): 138.4, 128.9, 124.7, 123.0, 122.2, 118.9<br>($CH_3$): 21.8, 16.5 |
| MS (mass spectroscopy) | — | — |

| Substituent | Ligand I species 23 |
|---|---|
| $R_{16}$ | 1-anthracenyl |
| $R_{17}$ | 1-anthracenyl |
| $R_{18}$ | $CH_3$ |
| $R_{19}$ | $CH_3$ |
| $R_{20}$ | H |
| $R_{21}$ | H |
| $R_{22}$ | H |
| M | — |
| X | — |
| n | — |
| Reference | 96 (Thesis p. 229) |
| $^1$H-NMR | 8.60–6.80(m, 27H), 2.12(s, 6H) |
| $^{13}$C-NMR | ($C_q$): 187.8, 165.5, 164.9, 162.2, 160.8, 151.5, 150.0, 145.9, 141.6, 140.2, 139.0, 132.8, 131.4, 130.5, 129.0, 128.9<br>(CH): 138.6, 136.8, 135.0, 132.0–129.1 ($5^x$CH), 127.2–123.7($7^x$CH), 121.1, 119.7, 108.8, 91.2, 89.8, 40.2<br>($CH_3$): 16.5 |
| MS (mass spectroscopy) | — |

TABLE II

| | Complex I Species | | | |
|---|---|---|---|---|
| Substituent | 24 | 25 | 26 | 27 |
| $R_1$ | $CH_3$ | $-CH_2CH_3$ | $-CH(CH_3)_2$ | $-C(CH_3)_3$ |
| $R_2$ | H | H | H | H |
| $R_3$ | H | H | H | H |
| $R_4$ | H | H | H | H |
| $R_5$ | H | H | H | H |
| $R_6$ | $CH_3$ | $-CH_2CH_3$ | $-CH(CH_3)_2$ | $-C(CH_3)_3$ |
| $R_7$ | H | H | H | H |
| $R_8$ | H | H | H | H |
| $R_9$ | H | H | H | H |
| $R_{10}$ | H | H | H | H |
| $R_{11}$ | $CH_3$ | $CH_3$ | $CH_3$ | $CH_3$ |
| $R_{12}$ | $CH_3$ | $CH_3$ | $CH_3$ | $CH_3$ |
| $R_{13}$ | H | H | H | H |
| $R_{14}$ | H | H | H | H |
| $R_{15}$ | H | H | H | H |
| M | V | V | V | V |
| X | Cl | Cl | Cl | Cl |
| n | 3 | 3 | 3 | 3 |
| Reference | 38110-21 | 38110-51 | 38110-64 | 38110-48 |

TABLE II-continued

| | Complex I Species | | | |
|---|---|---|---|---|
| Substituent | 28 | 29 | 30 | 31 |
| $R_1$ | $CH_3$ | $CH_3$ | $CH_3$ | $CH_3$ |
| $R_2$ | H | H | H | H |
| $R_3$ | H | H | H | H |
| $R_4$ | H | H | H | H |
| $R_5$ | $CH_3$ | $CH_3$ | $CH_3$ | $CH_3$ |
| $R_6$ | $CH_3$ | $CH_3$ | $CH_3$ | $CH_3$ |
| $R_7$ | H | H | H | H |
| $R_8$ | H | H | H | H |
| $R_9$ | H | H | H | H |
| $R_{10}$ | $CH_3$ | $CH_3$ | $CH_3$ | $CH_3$ |
| $R_{11}$ | H | $CH_3$ | $CH_3$ | $CH_3$ |
| $R_{12}$ | H | $CH_3$ | $CH_3$ | $CH_3$ |
| $R_{13}$ | H | H | H | H |
| $R_{14}$ | H | H | H | H |
| $R_{15}$ | H | H | H | H |
| M | V | V | V | V |

TABLE II-continued

| Substituent | | | | |
|---|---|---|---|---|
| X | Cl | Cl | Cl | Cl |
| n | 3 | 2 | 3 | 4 |
| Reference | — | — | 114 (Thesis, p. 144) | — |

| | Complex I Species | | | |
|---|---|---|---|---|
| Substituent | 32 | 33 | 34 | 35 |
| $R_1$ | $CH_3$ | $CH_3$ | $CH_3$ | $CH_3$ |
| $R_2$ | H | H | H | H |
| $R_3$ | H | H | H | H |
| $R_4$ | H | H | H | H |
| $R_5$ | $CH_3$ | $CH_3$ | $CH_3$ | $CH_3$ |
| $R_6$ | $CH_3$ | $CH_3$ | $CH_3$ | $CH_3$ |
| $R_7$ | H | H | H | H |
| $R_8$ | H | H | H | H |
| $R_9$ | H | H | H | H |
| $R_{10}$ | $CH_3$ | $CH_3$ | $CH_3$ | $CH_3$ |
| $R_{11}$ | $CH_3$ | $CH_3$ | $CH_3$ | $CH_3$ |
| $R_{12}$ | $CH_3$ | $CH_3$ | $CH_3$ | $CH_3$ |
| $R_{13}$ | H | H | H | H |
| $R_{14}$ | H | H | H | H |
| $R_{15}$ | H | H | H | H |
| M | V | Hf | Nb | Ta |
| X | Cl | Cl | Cl | Cl |
| n | 5 | 4 | 3 | 5 |
| Reference | — | — | — | — |

| | Complex I Species | | | |
|---|---|---|---|---|
| Substituent | 36 | 37 | 38 | 39 |
| $R_1$ | $CH_3$ | $CH_3$ | $CH_3$ | $CH_3$ |
| $R_2$ | H | H | H | H |
| $R_3$ | H | H | H | H |
| $R_4$ | H | H | H | H |
| $R_5$ | $CH_3$ | $CH_3$ | $CH_3$ | $CH_3$ |
| $R_6$ | $CH_3$ | $CH_3$ | $CH_3$ | $CH_3$ |
| $R_7$ | H | H | H | H |
| $R_8$ | H | H | H | H |
| $R_9$ | H | H | H | H |
| $R_{10}$ | $CH_3$ | $CH_3$ | $CH_3$ | $CH_3$ |
| $R_{11}$ | $CH_3$ | $CH_3$ | $CH_3$ | $CH_3$ |
| $R_{12}$ | $CH_3$ | $CH_3$ | $CH_3$ | $CH_3$ |
| $R_{13}$ | H | H | H | H |
| $R_{14}$ | H | H | H | H |
| $R_{15}$ | H | H | H | H |
| M | Mo | W | Cr | Ti |
| X | Cl | Cl | Cl | Cl |
| n | 6 | 6 | 3 | 3 |
| Reference | — | — | 111 (Thesis, p. 231) | 113 (Thesis, p. 231) |

| | Complex I Species | | | |
|---|---|---|---|---|
| Substituent | 40 | 41 | 42 | 43 |
| $R_1$ | $CH_3$ | —$CH(CH_3)_2$ | $CH_3$ | $CH_3$ |
| $R_2$ | H | H | H | H |
| $R_3$ | H | H | H | H |
| $R_4$ | H | H | Cl | $CH_3$ |
| $R_5$ | $CH_3$ | —$CH(CH_3)_2$ | H | H |
| $R_6$ | $CH_3$ | —$CH(CH_3)_2$ | $CH_3$ | $CH_3$ |
| $R_7$ | H | H | H | H |
| $R_8$ | H | H | H | H |
| $R_9$ | H | H | Cl | $CH_3$ |
| $R_{10}$ | $CH_3$ | —$CH(CH_3)_2$ | H | H |
| $R_{11}$ | $CH_3$ | $CH_3$ | $CH_3$ | $CH_3$ |
| $R_{12}$ | $CH_3$ | $CH_3$ | $CH_3$ | $CH_3$ |
| $R_{13}$ | H | H | H | H |
| $R_{14}$ | H | H | H | H |
| $R_{15}$ | H | H | H | H |
| M | Zr | V | V | V |

TABLE II-continued

| Substituent | | | | |
|---|---|---|---|---|
| X | Cl | Cl | Cl | Cl |
| n | 4 | 3 | 3 | 3 |
| Reference | — | 38110-62 | 38110-38 | 38110-57 |

| | Complex I Species | | | |
|---|---|---|---|---|
| Substituent | 44 | 45 | 46 | 47 |
| $R_1$ | $CH_3$ | $CH_3$ | $CH_3$ | $CH_3$ |
| $R_2$ | H | H | H | H |
| $R_3$ | Cl | Br | $CH_3$ | $CH_3$ |
| $R_4$ | H | H | H | H |
| $R_5$ | H | H | H | $CH_3$ |
| $R_6$ | $CH_3$ | $CH_3$ | $CH_3$ | $CH_3$ |
| $R_7$ | H | H | H | H |
| $R_8$ | Cl | Br | $CH_3$ | $CH_3$ |
| $R_9$ | H | H | H | H |
| $R_{10}$ | H | H | H | $CH_3$ |
| $R_{11}$ | $CH_3$ | $CH_3$ | $CH_3$ | $CH_3$ |
| $R_{12}$ | $CH_3$ | $CH_3$ | $CH_3$ | $CH_3$ |
| $R_{13}$ | H | H | H | H |
| $R_{14}$ | H | H | H | H |
| $R_{15}$ | H | H | H | H |
| M | V | V | V | V |
| X | Cl | Cl | Cl | Cl |
| n | 3 | 3 | 3 | 3 |
| Reference | 38110-41 | 38110-73 | 38110-54 | — |

| | Complex I Species | | | |
|---|---|---|---|---|
| Substituent | 48 | 49 | 50 | 51 |
| $R_1$ | $CH_3$ | $CH_3$ | $CH_3$ | H |
| $R_2$ | Cl | Br | $CH_3$ | H |
| $R_3$ | H | $CH_3$ | H | $CF_3$ |
| $R_4$ | H | H | H | H |
| $R_5$ | H | $CH_3$ | H | H |
| $R_6$ | $CH_3$ | $CH_3$ | $CH_3$ | H |
| $R_7$ | Cl | Br | $CH_3$ | H |
| $R_8$ | H | $CH_3$ | H | $CF_3$ |
| $R_9$ | H | H | H | H |
| $R_{10}$ | H | $CH_3$ | H | H |
| $R_{11}$ | $CH_3$ | $CH_3$ | $CH_3$ | $CH_3$ |
| $R_{12}$ | $CH_3$ | $CH_3$ | $CH_3$ | $CH_3$ |
| $R_{13}$ | H | H | H | H |
| $R_{14}$ | H | H | H | H |
| $R_{15}$ | H | H | H | H |
| M | V | V | V | V |
| X | Cl | Cl | Cl | Cl |
| n | 3 | 3 | 3 | 3 |
| Reference | 38110-30 | 38110-33 | 38110-42 | — |

| | Complex I Species | | |
|---|---|---|---|
| Substituent | 52 | 53 | 54 |
| $R_1$ | H | H | $CH_3$ |
| $R_2$ | H | H | H |
| $R_3$ | —$OCH_3$ | H | H |
| $R_4$ | H | H | H |
| $R_5$ | H | H | Br |
| $R_6$ | H | H | $CH_3$ |
| $R_7$ | H | H | H |
| $R_8$ | —$OCH_3$ | H | H |
| $R_9$ | H | H | H |
| $R_{10}$ | H | H | Br |
| $R_{11}$ | $CH_3$ | $CH_3$ | $CH_3$ |
| $R_{12}$ | $CH_3$ | $CH_3$ | $CH_3$ |
| $R_{13}$ | H | H | H |
| $R_{14}$ | H | H | H |
| $R_{15}$ | H | H | H |
| M | V | V | V |

TABLE II-continued

| X | Cl | Cl | Cl |
|---|----|----|----|
| n | 3 | 3 | 3 |
| Reference | — | 38110-67 | |

| Substituent | Complex I Species 55 |
|---|---|
| $R_{16}$ | —$CH_2$—$C_6H_5$ |
| $R_{17}$ | —$CH_2$—$C_6H_5$ |
| $R_{18}$ | $CH_3$ |
| $R_{19}$ | $CH_3$ |
| $R_{20}$ | H |
| $R_{21}$ | H |
| $R_{22}$ | H |

TABLE II-continued

| M | V |
|---|---|
| X | Cl |
| n | 3 |

TABLE III

| Complex Species (per Table II) | $M_n$ [g/mol] | $M_w$ [g/mol] | Polydispersity |
|---|---|---|---|
| 114 | 4,051 | 15,320 | 3.78 |
| 108 | 6,672 | 90,950 | 13.63 |
| 110 | 13,980 | 499,500 | 35.72 |

TABLE IV

| Rx Ref (NB) | Catalyst Description (Species) | Metal | Concentration (g Metal/mL × $10^{-4}$) |
|---|---|---|---|
| 9 | Tridentate, 2-Me (24) | Fe | 0.417 |
| 10 | Tridentate, 2-Me (24) | Fe | 0.835 |
| 11 | Tridentate, 2-Me (24) | Fe | 0.835 |
| 12 | Tridentate, 2-Me (24) | Fe | 1.16 |
| 13 | Tridentate, 2-Me (24) | Fe | 8.35 |
| 14 | Tridentate, 2-Me (24) | Fe | 1.16 |
| 15 | Tridentate, 2-Me (24) | Fe | 2.10 |
| 16 | Tridentate, 2-Me (24) | Fe | 1.67 |
| 17 | Tridentate, 2-Me (24) | Fe | 1.67 |
| 18 | Tridentate, 2-Me (24) | Fe | 1.67 |
| 19 | Tridentate, 2-Me (24) | Fe | 1.67 |
| 20 | Tridentate, 2-Me (24) | Fe | 1.67 |
| 21 | Tridentate, 2-Me (24) | V | 1.37 |
| 22 | Tridentate, 2-Me (24) | V | 1.37 |
| 23 | Tridentate, 2-Me (24) | V | 1.37 |
| 24 | Tridentate, 2-iPr (25) | V | 1.47 |
| 25 | Tridentate, 2-iPr (25) | V | 1.47 |
| 26 | Tridentate, 2-Me (24) | V | 1.37 |
| 27 | Tridentate, No Substitution (53) | V | 1.30 |
| 28 | Tridentate, No Substitution (53) | V | 1.30 |
| 29 | Tridentate, 2-Me (24) | V | 1.37 |
| 30 | Tridentate, 2-Me, 3 Cl (48) | V | 1.46 |
| 31 | Tridentate, 2-Me, 3 Cl (48) | V | 1.46 |
| 32 | Tridentate, 2-Me, 3 Cl (48) | V | 1.46 |
| 33 | Tridentate, 2,4,6-Me, 3 Br (49) | V | 1.74 |
| 34 | Tridentate, 2,4,6-Me, 3 Br (49) | V | 1.74 |

| Rx Ref (NB) | Catalyst to $R_x$ (mL) | Co-Catalyst | Co-cat/CAT ratio | Run time (min) |
|---|---|---|---|---|
| 9 | 10 | MAO | 2,000 | 30 |
| 10 | 5 | MAO | 10,000 | 30 |
| 11 | 20 | MAO | 10,000 | 30 |
| 12 | 10 | MMAO | 2,000 | 60 |
| 13 | 8.5 | MAO | 100 | 30 |
| 14 | 10 | MMAO | 2,000 | 30 |
| 15 | 20 | MAO | 400 | 30 |
| 16 | 2.5 | MAO | 500 | 30 |
| 17 | 2.5 | MAO | 500 | 30 |
| 18 | 2.5 | MAO | 500 | 30 |
| 19 | 2.5 | MAO | 500 | 30 |
| 20 | 2.5 | MAO | 500 | 30 |
| 21 | 3 | MAO | 500 | 30 |
| 22 | 1.5 | MAO | 500 | 30 |
| 23 | 1.5 | MAO | 500 | 30 |
| 24 | 1.5 | MAO | 500 | 30 |
| 25 | 10 | MAO | 500 | 30 |
| 26 | 1.5 | MAO | 500 | 30 |
| 27 | 1.5 | MAO | 500 | 30 |
| 28 | 10 | MAO | 500 | 30 |
| 29 | 1.5 | MAO | 500 | 30 |
| 30 | 1.5 | MAO | 500 | 30 |
| 31 | 1.5 | MAO | 500 | 30 |
| 32 | 1.5 | MAO | 500 | 30 |

TABLE IV-continued

| | | | | | |
|---|---|---|---|---|---|
| 33 | 1.5 | MAO | 500 | 30 | |
| 34 | 1.5 | MAO | 500 | 30 | |

| Rx Ref (NB) | R Temp (C.) | $R_x$ Press (psig) | $H_2$ (psig) |
|---|---|---|---|
| 9 | 60 | 315 | 50 |
| 10 | 60 | 315 | 50 |
| 11 | 60 | 315 | 50 |
| 12 | 60 | 315 | 50 |
| 13 | 60 | 315 | 50 |
| 14 | 60 | 315 | 50 |
| 15 | 60 | 315 | 50 |
| 16 | 60 | 315 | 0 |
| 17 | 60 | 315 | 50 |
| 18 | 60 | 315 | 0 |
| 19 | 60 | 315 | 50 |
| 20 | 60 | 315 | 0 |
| 21 | 60 | 250 | 0 |
| 22 | 60 | 250 | 0 |
| 23 | 60 | 250 | 0 |
| 24 | 60 | 250 | 0 |
| 25 | 60 | 250 | 0 |
| 26 | 60 | 250 | 0 |
| 27 | 60 | 250 | 0 |
| 28 | 60 | 250 | 0 |
| 29 | 60 | 250 | 0 |
| 30 | 60 | 250 | 0 |
| 31 | 60 | 250 | 50 |
| 32 | 60 | 250 | 0 |
| 33 | 60 | 250 | 0 |
| 34 | 60 | 250 | 50 |

| Rx Ref (NB) | $CH_2$ = uptake | Solids (g) | Metal to Rx (g) | Wt. % liquid | Polymer Productivity (g. polymer per g. transition metal) | Oligomer Produc-tivity (g. oligomer per g. transition metal) | 1-Hexene Purity (wt %) |
|---|---|---|---|---|---|---|---|
| 9 | 3.4 | 2.51 | 0.00042 | 26.2 | 5,980 | 2,120 | na |
| 10 | 4.1 | na | 0.00042 | na | na | 9,760 | na |
| 11 | 3.3 | na | 0.00168 | na | na | 1,960 | na |
| 12 | 18.3 | na | 0.00116 | na | na | 15,800 | na |
| 13 | 30.1 | 4.12 | 0.00714 | 86.3 | 580 | 3,640 | na |
| 14 | 7.2 | 3.105 | 0.00116 | 56.9 | 2,680 | 3,530 | na |
| 15 | 35.4 | na | 0.0042 | na | na | 8,430 | na |
| 16 | 28.9 | 1.8873 | 0.00042 | 93.5 | 4,490 | 64,300 | na |
| 17 | 22 | 1.3756 | 0.00042 | 93.7 | 3,280 | 49,100 | na |
| 18 | 262.6 | na | 0.00042 | na | na | 625,000 | na |
| 19 | 52.5 | na | 0.00042 | na | na | 125,000 | na |
| 20 | 64.9 | na | 0.00042 | na | na | 155,000 | na |
| 21 | 134.2 | 1.6932 | 0.00041 | 98.7 | 4,130 | 323,000 | 94.0 |
| 22 | 127.6 | 0.9603 | 0.00021 | 99.2 | 4,570 | 603,000 | 95.2 |
| 23 | 135.8 | 1.4884 | 0.00021 | 98.9 | 7,080 | 639,000 | 94.7 |
| 24 | 10.2 | 2.33 | 0.00022 | 77.2 | 10,590 | 35,800 | na |
| 25 | 39.1 | 15.987 | 0.00147 | 59.1 | 10,880 | 15,700 | 96.8 |
| 26 | na | 1.9236 | 0.00021 | na | 9,160 | na | 96.3 |
| 27 | 13.5 | 1.0534 | 0.0002 | 92.2 | 5,270 | 62,200 | na |
| 28 | 21.4 | 7.2206 | 0.0013 | 66.3 | 5,550 | 10,910 | 91.7 |
| 29 | 132 | 0.6946 | 0.00021 | 99.5 | 3,310 | 625,000 | 97.0 |
| 30 | 246.9 | 2.1282 | 0.00022 | 99.1 | 9,670 | 1,110,000 | 94.4 |
| 31 | 245.3 | 0.5757 | 0.00022 | 99.8 | 2,620 | 1,110,000 | 83.0 |
| 32 | 175.4 | 2.4043 | 0.00022 | 98.6 | 10,930 | 786,000 | 94.0 |
| 33 | 69.4 | 32.97 | 0.00026 | 52.5 | 126,810 | 140,000 | 88.8 |
| 34 | 25.3 | 17.33 | 0.00026 | 31.5 | 66,650 | 30700 | na |

TABLE V

| $R_x$ Ref | V MAO 500 0 2-Me | V MAO 500 0 2-Me | V MAO 500 0 2-Me | V MAO 500 0 2-iPr |
|---|---|---|---|---|
| $C_4$ | 1.94875 | 2.87902 | 1.50178 | 0.02694 |
| $C_6$ | 5.25913 | 5.52978 | 4.69127 | 0.06112 |
| $C_8$ | 4.11861 | 4.11093 | 3.57549 | 0.04962 |
| $C_{10}$ | 3.02258 | 2.64948 | 2.60784 | 0.31937 |
| $C_{12}$ | 1.07445 | 1.22068 | 0.81371 | 0.6178 |
| $C_{14}$ | 0.68739 | 0.5995 | 0.41228 | 1.13829 |
| Total | 16.11391 | 16.98939 | 13.60237 | 2.21314 |

| $R_x$ Ref | V MAO 500 0 2-iPr | V MAO 500 0 2-Me | V MAO 500 0 No Sub | V MAO 500 0 No Sub |
|---|---|---|---|---|
| $C_4$ | 0.26597 | 1.42813 | 0.0412 | 0.21023 |
| $C_6$ | 0.62009 | 4.56894 | 0.05981 | 0.17499 |
| $C_8$ | 0.53036 | 6.6156 | 0.02102 | 0.05842 |
| $C_{10}$ | 0.38063 | 2.4048 | 0.40742 | 0.33275 |
| $C_{12}$ | 0.2384 | 1.17217 | 0.83135 | 0.02193 |
| $C_{14}$ | 0.16143 | 0.59551 | 0.50959 | 0.001 |
| Total | 2.19688 | 16.78515 | 1.87039 | 0.80832 |

| $R_x$ Ref | V MAO 500 0 2-Me | V MAO 500 0 2-Me, 3-Cl | V MAO 500 0 2-Me, 3-Cl | V MAO 500 0 2-Me, 3Cl |
|---|---|---|---|---|
| $C_4$ | 2.50098 | 3.67261 | 2.96306 | 3.50596 |
| $C_6$ | 4.57281 | 6.29733 | 6.25049 | 5.90836 |
| $C_8$ | 3.15371 | 4.24057 | 5.12474 | 4.06233 |
| $C_{10}$ | 1.96705 | 2.30421 | 3.58522 | 2.37831 |
| $C_{12}$ | 0.94216 | 0.77521 | 0.88542 | 0.84284 |
| $C_{14}$ | 0.43252 | 0.2402 | 0.37585 | 0.27303 |
| Total | 13.56923 | 17.53013 | 19.18478 | 16.97083 |

| Rx Ref | V MAO 500 0 2,4,6-Me, 3-Br | V MAO 500 0 2,4,6-Me, 3-Br |
|---|---|---|
| $C_4$ | 0.11393 | 0.04003 |
| $C_6$ | 0.29025 | 0.10934 |
| $C_8$ | 0.22473 | 0.11979 |
| $C_{10}$ | 0.21288 | 0.08425 |

TABLE V-continued

| | | |
|---|---|---|
| $C_{12}$ | 0.10839 | 0.08109 |
| $C_{14}$ | 0.08277 | 0.07155 |
| Total | 1.03295 | 0.50605 |

That which is claimed is:

1. A polymerization process comprising: contacting under polymerizing conditions in a reaction zone:
   a. at least one olefin; and
   b. at least one catalyst having one of the following structures:

Complex I

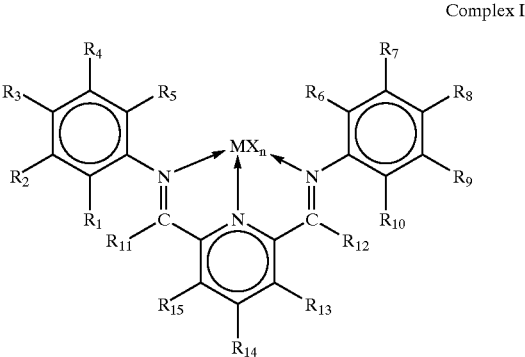

Complex II

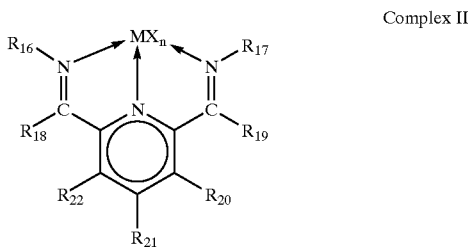

wherein:
$R_1-R_{22}$ are independently selected from halogen; nitrile or isonitrile; cyanate or isocyanate; straight or branched chain alkyl, alkenyl, alkynyl, cycloalkyl, aryl, aralkyl, alkaryl moieties or combinations thereof, any of which optionally include substituent or linking heteroatoms of halogen, oxygen, nitrogen, silicon, phosphorus or sulfur;
M is a metal selected from Group 4b, 5b or 6b transition metals;
X is an anion; and
n is 2, 3, 4, 5 or 6.

* * * * *